US006886198B2

(12) United States Patent
Marin et al.

(10) Patent No.: US 6,886,198 B2
(45) Date of Patent: May 3, 2005

(54) METHOD AND APPARATUS FOR POSITIONING THE ARM OF A PATIENT WHILE ON A TABLE FOR A MEDICAL PROCEDURE ON A BREAST

(75) Inventors: Peter Marin, Kanata (CA); Luc Corbeil, Ste-Anne-des-Lacs (CA)

(73) Assignee: ART Advanced Research Technologies Inc., Saint-Laurent (CA)

( * ) Notice: Subject to any disclaimer, the term of this patent is extended or adjusted under 35 U.S.C. 154(b) by 0 days.

(21) Appl. No.: 10/317,215

(22) Filed: Dec. 12, 2002

(65) Prior Publication Data

US 2004/0111801 A1 Jun. 17, 2004

(51) Int. Cl.⁷ .................................................. A61B 6/04
(52) U.S. Cl. .................... 5/601; 5/622; 5/623; 378/209
(58) Field of Search .......................... 5/601, 621, 622, 5/623, 735; 378/37, 180, 209

(56) References Cited

U.S. PATENT DOCUMENTS

| | | | |
|---|---|---|---|
| 3,165,630 A | | 1/1965 | Bielat et al. |
| 3,973,126 A | * | 8/1976 | Redington et al. ............ 378/17 |
| 5,297,303 A | * | 3/1994 | Stafford et al. ................. 5/613 |
| 5,409,497 A | | 4/1995 | Siczek et al. |
| 5,415,169 A | | 5/1995 | Siczek et al. |
| 5,564,438 A | | 10/1996 | Merchant |
| 5,569,266 A | | 10/1996 | Siczek |
| 5,609,152 A | * | 3/1997 | Pellegrino et al. ........... 600/429 |
| 5,855,554 A | * | 1/1999 | Schneider et al. ........... 600/407 |
| 6,419,390 B1 | * | 7/2002 | Landis-Lowell ............. 378/209 |
| 2002/0056161 A1 | * | 5/2002 | Falbo et al. ................... 5/601 |

FOREIGN PATENT DOCUMENTS

| | | |
|---|---|---|
| EP | 0 845 242 A2 | 6/1998 |
| FR | 2 653 005 | 4/1991 |
| GB | 2 277 664 A | 6/1993 |
| WO | WO 98/55013 | 12/1998 |
| WO | WO01/35829 | 5/2001 |

* cited by examiner

Primary Examiner—Michael Trettel
(74) Attorney, Agent, or Firm—Alexandra Daoud; James Anglehart; Ogilvy Renault

(57) ABSTRACT

A table is provided for positioning a patient for a medical procedure on a breast, the table comprising: a supporting platform having a back end for supporting the patient's legs and a front end for supporting the patient's torso while the patient is in a prone position, and a cavity at the front end for allowing the breast and a surrounding axilla region to be pendantly suspended therethrough; and an armrest for positioning and supporting a forearm such that a shoulder adjacent to the axilla region is at a desired height, wherein the armrest is lower than the platform.

13 Claims, 3 Drawing Sheets

METHOD AND APPARATUS FOR POSITIONING THE ARM OF A PATIENT WHILE ON A TABLE FOR A MEDICAL PROCEDURE ON A BREAST

CROSS-REFERENCE TO RELATED APPLICATION

This application is related to US patent application entitled "Table for Positioning a Patient for a Medical Procedure on a Breast" filed simultaneously herewith and with Ser. No. 10/306,724, the specifications of which is hereby incorporated by reference. The application is also related to US patent applications entitled "Method and Apparatus for Positioning a patient on a Table for a Medical Procedure on a Breast" and "Method and Apparatus for Optical Imaging" filed on Nov. 8, 2002 and with Ser. No. 10/290,476 and 10/290,485, respectively, the specifications of which are hereby incorporated by reference.

FIELD OF THE INVENTION

The invention relates to a table for positioning a patient when performing breast imaging, scanning, and biopsies. More specifically, it relates to placing the arm of a patient undergoing a procedure on a breast such that the patient is comfortable and the position of the breast is ideal for the medical procedure.

BACKGROUND OF THE INVENTION

Certain medical procedures, such as breast biopsies, must be done with the patient in a face down prone position. There are also imaging and scanning procedures that are done in a prone position.

Research has shown that a large proportion of breast tumors are found in the axilla region. For this reason, many new designs of tables for medical procedures on breasts, whether these procedures be imaging of the breast or breast biopsies, have specially shaped cavities to receive the breast and the surrounding axilla region.

However, an important factor to the volume of tissue accessible to medical equipment below a table is the position of the arm of the patient. The position of the arm has an influence on the position of the breast and axilla in the cavity. It also has an impact on the comfort level experienced by the patient, who must remain in a substantially immobile position for an extensive period of time.

Moreover, since positioning of the patient on the table is of great importance to the success of the medical procedure on the breast, there is a need to improve the current designs of the tables in order to obtain the best results possible.

SUMMARY OF THE INVENTION

Accordingly, an object of the present invention is to position the patient on a table for a procedure on a breast such that the patient is comfortable.

Another object of the invention is to position the arm of the patient such that a maximum volume of tissue is exposed via a cavity in the table.

According to a first broad aspect of the present invention, there is provided a table for positioning a patient for a medical procedure on a breast, the table comprising: a supporting platform having at least a front end for supporting the patient's torso while the patient is in a prone position, and a cavity at the front end for allowing the breast and a surrounding axilla region to be pendantly suspended therethrough; and an armrest for positioning and supporting a forearm such that a shoulder adjacent to the axilla region is at a desired height, wherein the armrest is lower than the platform.

Preferably, the table also comprises a lateral depression for allowing an arm and a shoulder adjacent to the breast to extend over the table, rest on the armrest, and be lowered such that breast tissue from the axilla region is relaxed and extends through the cavity. The table is configured such that the lateral depression is provided on the left and right side of the table, depending on which breast is undergoing the medical procedure.

Also preferably, a substantially pear-shaped cavity is provided such that the axilla region is more easily accessible. The pear-shaped cavity is oriented such that the narrow portion is facing towards the outside of the table while the larger portion is facing the inside of the table. The table is configured such that the cavity can be rotated laterally to follow the side on which the lateral depression is provided.

According to a second broad aspect of the present invention, there is provided a method for positioning a patient on a table for a medical procedure on a breast, the method comprising: placing the patient face down in a prone position on a supporting platform such at least said patient's torso is supported; providing a cavity in the supporting platform such that the breast and a surrounding axilla region are pendantly suspended therethrough; and positioning an arm of the patient adjacent to the breast on an armrest such that a shoulder is at a desired height and such that the patient is comfortable while a maximum volume of the axilla region is exposed through the cavity.

Preferably, the armrest is provided parallel to the supporting platform. Alternatively, the armrest can be provided below a headrest, allowing the arm to be extended upwards and bent inwards on the armrest.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

Figure 1:
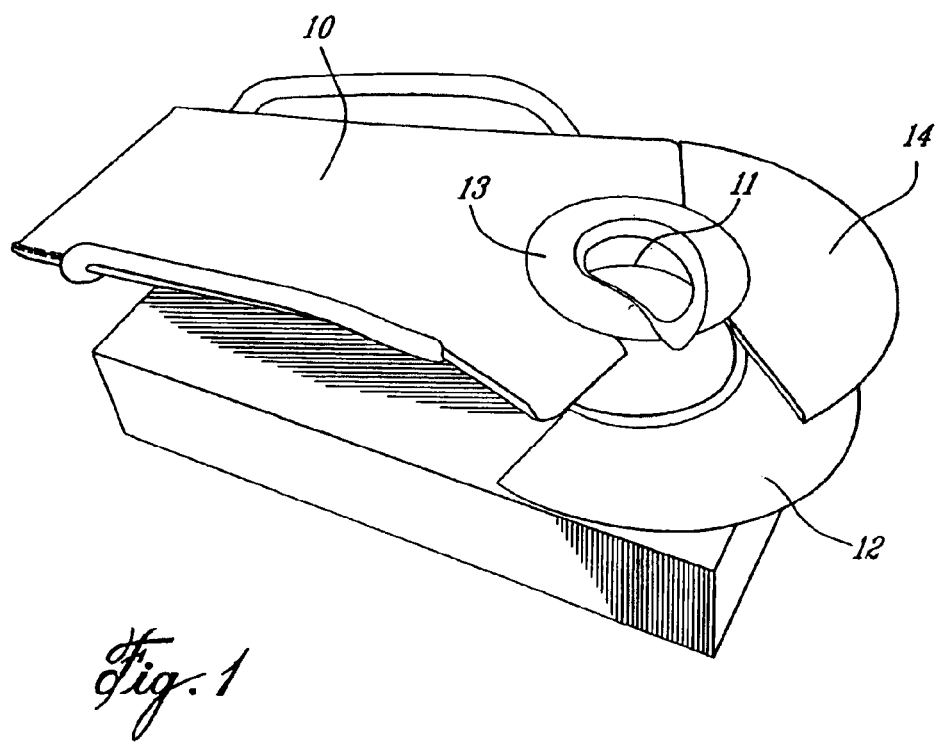
FIG. 1 is a first embodiment of the table according to the invention.

FIG. 1 shows a preferred embodiment for the table. The table comprises a supporting platform 10 having a back end and a front end for supporting the patient's legs and torso, respectively. The patient lies face down on the table, slightly off center, and places a breast inside the cavity 11 present in the front end of the supporting platform 10. The breast is pendantly suspended within the cavity 11. The table has a lateral depression for allowing the arm and shoulder adjacent to the breast to extend over the table. Note that the supporting platform may be only half the length shown in the figure, such that only the torso is supported. The patient would then be standing or kneeling next to the platform while being bent at the waist and having her torso supported by the shortened platform with the breast suspended in the cavity. Therefore, the term prone position is to be understood as meaning that at least the upper body is in a prone position.

The armrest 12 shown in FIG. 1 is lower than the supporting platform 10. The patient's arm extends over the table through the space provided and rests on the armrest 12. The arm is extended upwards and bent inwards, the elbow and forearm resting on the surface of the armrest 12. The position of the elbow on the surface is adjusted such that the shoulder adjacent the arm is at a desired height for comfort and for allowing a maximum volume of tissue of the breast and axilla region to be pendantly suspended through the cavity 11. The lateral position of the arm with respect to the body is also important. Extending the arm away from the body stretches the skin and pulls tissue out of the cavity. Having the arm close to the body allows the skin to stay relaxed and the breast and axilla tissue to conform more easily to the shape of the cavity 11.

The armrest 12 is adjustable in height to accommodate patients of different sizes and place the shoulder at the ideal level so that the patient is comfortable enough to remain in a fixed position for a substantially long amount of time.

In order to maintain the arm in a fixed position after it has been placed on the armrest, various structures may be used. For example, choosing a material for the top surface of the armrest with a relatively high coefficient of friction ensures that the arm will not slip off once it has been positioned. Alternatively, abutment means may be placed on the outer edges of the armrest to prevent the arm from slipping off the top surface. The abutment means may be adjustable in relative width to clamp the arm into the right position and prevent additional lateral motion. Yet another alternative is to have the surface of the armrest be a cushion. Once pressure is applied to the cushion by the forearm, the indentation formed is sufficient to prevent any unwanted motion by the arm along the surface of the armrest.

In the embodiment shown in FIG. 1, the cavity 11 is substantially pear-shaped. That is to mean that the cavity 11 comprises a wide and a narrow portion, such that the wide portion is for the breast to be suspended therethrough and the narrow portion is for the axilla region adjacent to the breast to be suspended therethrough. The shape of the cavity 11 is such that a maximum possible volume of tissue can be exposed below the table. This way, access to the regions of interest is facilitated.

The table shown in FIG. 1 can be used to perform a medical procedure on a left or a right breast. The cavity 11 is present in a disc plate 13 in the front end of the supporting platform 10. For imaging of the left breast, the cavity 11 must be rotated such that the narrow portion is facing towards the left side of the table in order to receive the left axilla region of the patient. The rotation of the disc 13 can be done manually or remotely with a set of controls. The headrest 14 must also be moved such that the space provided for the arm of the patient is on the left side of the table. As can be seen from FIG. 1, the headrest 14 is independent of the supporting platform 10 and can be slid to the opposite side. This can also be done either manually or remotely with a set of controls.

The table is slightly inclined such that the legs and feet are at a lower level than the head and torso. This is also for patient comfort and provides the patient with a better sense of stability in the prone position.

Figure 2:
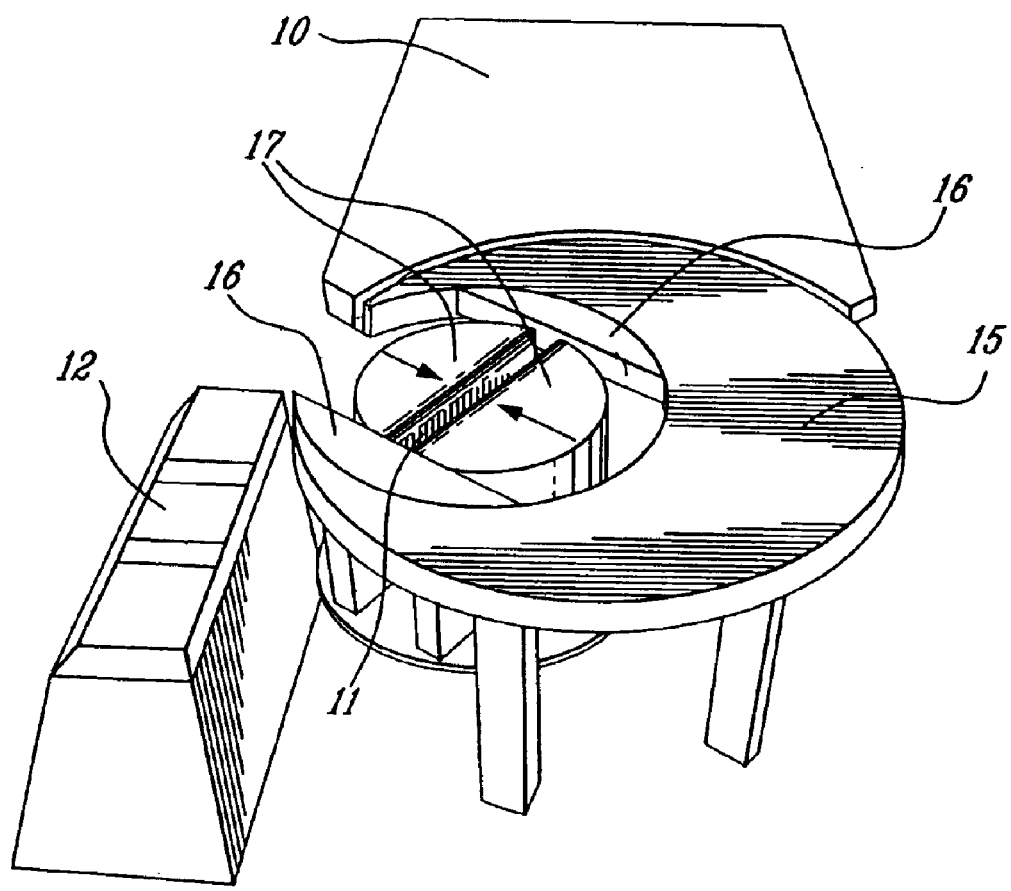
FIG. 2 is a second embodiment of the table according to the invention.

FIG. 2 shows an alternative embodiment to providing a space for the arm on a left and a right side of the table. A supporting platform 10 is still present to support the legs and torso of the patient. However, a large disc 15 is engaged into the supporting platform 10. Within this large disc 15 is a smaller disc 16 with the cavity 11 for the breast. The larger disc 16 rotates such that the opening for the arm is on the left or the right side of the table, depending on the breast in question. The cavity 11 for the breast is closer to the side than in the previous embodiment, shown in FIG. 1.

The armrest 12 seen in the figure is parallel to the supporting platform 10. The arm corresponding to the breast undergoing the medical procedure is rested on the armrest 12 such that the elbow and forearm are in contact with the surface of the armrest 12. In this case, the armrest 12 can be adjusted in height to accommodate patient's of different sizes, as well as in position with respect to the distance of the armrest 11 from the supporting platform 10. The armrest 10 can also be angled such that it is at an angle from the supporting platform 10, having either its front end or back end further away from the table.

The design of the smaller disc 16 is such that the breast can be scanned or imaged in all directions between −90° and +90°. To reproduce X-Ray mammography standard views, two parallel, vertical, stabilizing plates compress the breast at 0° (the plates move along the axes of the table), 90° (the plates move perpendicular to the axes of the table), and 45° (the plates move diagonally). The plates, which are seen as two compression members 17 in the figure, form a rectangular cavity 11 and can accommodate breasts of varying sizes. The two members 17 can move inwards for compression, as well as up, down, and rotating with respect to the rest of the platform 10. The smaller disc 16 is formed of at least two separate pieces that surround the cavity 11. One of the pieces can be removed to leave a space for the axilla and underarm region, providing a lateral depression on a left or a right side of the table, depending on the position of the larger disc 15. An armrest 12 is also present to support the forearm and elbow when the axilla region is exposed through the cavity 11.

The design of the larger disc 15 is possible without the smaller disc 16 within it. A regular cavity is present within the larger disc, the cavity being fixed in size and shape (not shown). This embodiment can be used for biopsies, wherein it is unnecessary to compress the breast at different angles because images are not being taken of the breast. The biopsy equipment can easily be placed underneath the table and used in conjunction with it.

Alternatively, a pear-shaped cavity may be present in the larger disc (not shown). The cavity is to be angled at approximately 45° below the horizontal axis of the disc. When the disc is rotated, the cavity is still angled at approximately 45° of the horizontal axis, but on the opposite side of the table. In this case, compression plates may be independent from the table and be provided beneath the table. A space adjacent to the cavity is to be provided for the arm within the larger disc if the smaller disc is not within the larger disc plate.

It can be appreciated that armrests may be provided adjacent to standard tables for medical procedures on breasts even when lateral depressions are not provided for the arm. In this case, it is advantageous for the breast cavity to be located close to the edge of the table so that the arm and shoulder adjacent to the breast in the cavity may come down over the edge of the table and reside on the armrest.

Figure 3:
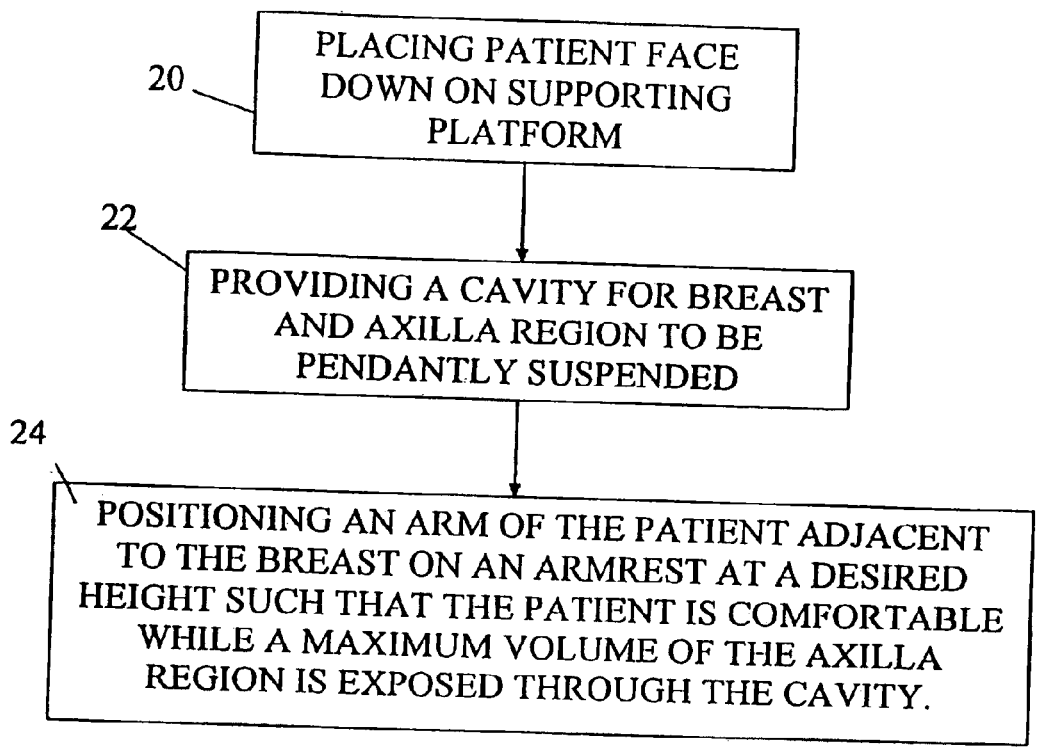
FIG. 3 is a flowchart of the method according to the invention.

FIG. 3 is a flowchart of the method according to the present invention. The first step of the method is to place a patient face down on a supporting platform 20. The supporting platform may take various forms, such as those described above or other possible embodiments known to a person skilled in the art. The next step is to provide a cavity for a breast and a surrounding axilla region to be pendantly suspended therethrough 22. The method then comprises positioning an arm of the patient adjacent to the breast on an armrest at a desired height such that the patient is comfortable while a maximum volume of the axilla region is exposed through the cavity 24.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A table for positioning a patient for a medical procedure on a breast, the table comprising:
   a supporting platform having at least a front end for supporting said patient's torso while said patient is in a prone position, and a cavity at said front end for allowing said breast and a surrounding axilla region to be pendantly suspended therethrough; and
   an armrest for positioning and supporting a forearm such that a shoulder adjacent to said axilla region is at a desired height, wherein said armrest is lower than said platform, and wherein said platform has a lateral depression for allowing an arm and a shoulder adjacent to said breast to extend over said platform, rest on said armrest, and be lowered such that skin from said axilla region is relaxed and extends through said cavity.

2. A table as claimed in claim 1, wherein said armrest comprises a structure for immobilizing said arm such that said arm is maintained in a fixed position.

3. A table as claimed in claim 1, wherein said table is configured to provide said depression on each side of said cavity in a position where a right shoulder would be when a right breast is in the cavity and a left shoulder would be when a left breast is in the cavity.

4. A table as claimed in claim 3, wherein said supporting platform further comprises a disc plate engaged into said front end and housing said cavity, said disc plate pivotable about an axis such that said lateral depression is provided on a left side of said table when a left breast is in said cavity and on a right side of said table when a right breast is in said cavity.

5. A table as claimed in claim 4, wherein said disc plate further comprises a smaller disc plate housing said cavity, wherein said smaller disc plate is adjacent to said lateral depression and is provided on a left side of said table when a left breast is in said cavity and on a right side of said table when a right breast is in said cavity, and said smaller disc plate is moveable about a plurality of axes independently from said disc plate such that said cavity is adjustable in position and size.

6. A table as claimed in claim 5, wherein said smaller disc plate is comprised of two compression members having linear movement relative to each other for adjusting said cavity in size, at least one of said compression members is removable to provide said lateral depression, and wherein said compression members have linear movement relative to said disc plate.

7. A table for positioning a patient for a medical procedure on a breast, the table comprising:
   a supporting platform having at least a front end for supporting said patient's torso while said patient is in a prone position, and a cavity at said front end for allowing said breast and a surrounding axilla region to be pendantly suspended therethrough; and
   an armrest for positioning and supporting a forearm such that a shoulder adjacent to said axilla region is at a desired height, wherein said armrest is lower than said platform, and wherein said armrest comprises material covering a surface of said armrest and having a friction coefficient such that said arm remains in a position in which it is placed.

8. A table for positioning a patient for a medical procedure on a breast, the table comprising:
   a supporting platform, having at least a front end for supporting said patient's torso while said patient is in a prone position, and a cavity at said front end for allowing said breast and a surrounding axilla region to be pendantly suspended therethrough; and
   an armrest for positioning and supporting a forearm such that a shoulder adjacent to said axilla region is at a desired height, wherein said armrest is lower than said platform, wherein said armrest is adjustable in height and position with respect to said supporting platform.

9. A table as claimed in claim 8, wherein said armrest is fixed with respect to a base and said supporting platform is adjustable in height.

10. A table for positioning a patient for a medical procedure on a breast, the table comprising:
    a supporting platform having at least a front end for supporting said patient's torso while said patient is in a prone position, and a cavity at said front end for allowing said breast and a surrounding axilla region to be pendantly suspended therethrough; and
    an armrest for positioning and supporting a forearm such that a shoulder adjacent to said axilla region is at a desired height, wherein said armrest is lower than said platform;
    wherein said cavity is substantially pear-shaped such that a larger portion is for the breast and a narrower portion is for the axilla region, and said cavity is positioned at an angle such that said narrower portion faces an outer side of said table.

11. A table as claimed in claim 10, wherein said table is configured such that said pear-shaped cavity is displaced to provide said narrower portion on a left side of said table when a left breast is in said cavity and on a light side of said table when a right breast is in said cavity.

12. A table for positioning a patient for a medical procedure on a breast, the table comprising:
    a supporting platform having at least a front end for supporting said patient's torso while said patient is in a prone position, and a cavity at said front end for allowing said breast and a surrounding axilla region to be pendantly suspended therethrough;
    an armrest for positioning and supporting a forearm such that a shoulder adjacent to said axilla region is at a desired height, wherein said armrest is lower than said platform; and
    a headrest adjacent to said front end for supporting a head of said patient while in said prone position, wherein said headrest is at a same height as said supporting platform.

13. A table as claimed in claim 12, wherein said headrest is configured to be laterally displaceable with respect to said supporting platform.

* * * * *